United States Patent [19]

Anastasio

[11] 4,361,155
[45] Nov. 30, 1982

[54] BLOOD SAMPLING UNIT

[76] Inventor: Frank W. Anastasio, 833 Packard Ave., Louisville, Ky. 40217

[21] Appl. No.: 201,991

[22] Filed: Oct. 29, 1980

[51] Int. Cl.³ .............................................. A61B 5/14
[52] U.S. Cl. .................................... 128/763; 128/765; 128/766
[58] Field of Search ............................... 128/763–766, 128/218 P, 218 PA, 218 M, 760, 771, 278; 73/864.16

[56] References Cited

U.S. PATENT DOCUMENTS

| | | | |
|---|---|---|---|
| 2,102,785 | 12/1937 | Brooks | 128/763 |
| 2,798,487 | 7/1957 | Ferguson | 128/218 P |
| 3,166,993 | 1/1965 | Blenkle | 128/218 P |
| 3,433,216 | 3/1969 | Mattson | 128/764 |
| 3,566,859 | 3/1971 | Schwartz | 128/765 |
| 3,577,980 | 5/1971 | Cohen | 128/765 |
| 3,596,652 | 8/1971 | Winkelman | 128/762 |
| 3,707,968 | 1/1973 | Koenig | 128/218 PA |
| 3,753,432 | 8/1973 | Guerra | 128/764 |
| 3,785,367 | 1/1974 | Tortin et al. | 128/763 |
| 3,809,298 | 5/1974 | Harris, Sr. et al. | 128/218 P |
| 3,901,219 | 8/1975 | Kay | 128/764 |
| 3,930,491 | 1/1976 | Hatsuno et al. | 128/765 |
| 3,931,815 | 1/1976 | Takatsuki | 128/764 |
| 3,943,917 | 3/1976 | Johangen | 128/763 |
| 3,960,139 | 6/1976 | Bailey | 128/762 |
| 3,965,889 | 6/1976 | Sachs | 128/762 |
| 3,978,846 | 9/1976 | Bailey | 128/762 |
| 3,985,122 | 10/1976 | Topham | 128/765 |
| 4,041,934 | 8/1977 | Genese | 128/763 |
| 4,050,451 | 9/1977 | Columbus | 128/764 |
| 4,055,177 | 10/1977 | Cohen | 128/218 M |
| 4,057,052 | 11/1977 | Kaufman et al. | 128/765 |
| 4,065,360 | 12/1977 | Kreb | 128/218 M |
| 4,133,304 | 1/1979 | Bailey | 128/764 |
| 4,159,713 | 7/1979 | Prais | 128/765 |
| 4,206,768 | 6/1980 | Bailey | 128/763 |
| 4,212,309 | 7/1980 | Moorehead | 128/766 |
| 4,215,702 | 8/1980 | Ayer | 128/766 |
| 4,235,235 | 11/1980 | Bekkering | 128/218 P |
| 4,244,379 | 1/1981 | Smith | 128/766 |
| 4,257,426 | 3/1981 | Bailey | 128/218 PA |
| 4,287,819 | 9/1981 | Emerit | 128/765 |

FOREIGN PATENT DOCUMENTS

| | | | |
|---|---|---|---|
| 161078 | 11/1953 | Australia | 128/218 PA |
| 2358493 | 11/1973 | Fed. Rep. of Germany | 128/764 |
| 2603777 | 8/1976 | Fed. Rep. of Germany | 128/764 |

Primary Examiner—Kyle L. Howell
Assistant Examiner—Nancy A. B. Swisher
Attorney, Agent, or Firm—Wm. R. Price

[57] ABSTRACT

A blood sampling unit having a barrel member consisting of a calibrated tubular body which is reduced at one end to form a projecting hollow neck for provision of a hollow needle containing a floating stopper and a slideable plunger. The plunger has an axially disposed gas channel in communication with the barrel and an orifice at its distal end. The unit is designed so that a supply of liquid or dry anticoagulant can be introduced into the portion of the projecting neck extending between the stopper and the needle. Alternately, the heparin or other anticoagulant can be obtained from a vial by drawing the heparin through the hollow needle and into the syringe proper. The plunger acts as a stop so that when its proximal end is set at the proper calibration for the desired sample, arterial blood pressure will move the floating stopper into abutment with the proximal end of the plunger while evacuating residual air through the axially disposed gas channel.

7 Claims, 8 Drawing Figures

BLOOD SAMPLING UNIT

FIELD OF THE INVENTION

This invention relates to a blood sampling unit for sampling blood for purposes of blood gas analysis. More simply stated, this invention relates to a blood sampling unit for collecting a sample of blood from the patient without contamination of the blood sample with air.

BACKGROUND OF THE INVENTION

For the purpose of learning the condition of the pneumatic function and electrolyte metabolism of the human body, measurement must be made by blood gas analysis of the respective amounts of oxygen saturation of pH of the arterial blood. Quantitative tests for the electrolyte components in blood may be made simultaneously. In such a blood test, contact of the blood sample to be tested with air or the incorporation of air into the blood sample has an undesirable effect upon the measured value in that the measured value is altered from the true condition of the arterial blood. In its simplest aspects, blood gas analysis is primarily a measurement of $PO_2$ and $PCO_2$ in the arterial blood. In this context, the P stands for the partial pressure of the particular gas in the blood. Additionally, a pH determination is usually made. This is a "STAT" procedure. If any time at all elapses between collection and processing, the sample must be iced. Contact of the sample with air has two effects. In the first place, the contact of the sample with oxygen will tend to increase the $PO_2$ reading. Simultaneously, some of the $CO_2$ in the blood sample may be lost and this will lower the $PCO_2$ reading. In short, contamination of the blood sample with air makes a disproportionate change in the results obtained by raising the $PO_2$ reading and lowering the $PCO_2$ reading. Normally, an anticoagulant such as heparin is utilized to prevent coagulation of the sample in the shank portion of the needle or in the syringe proper. Additionally, the anticoagulant has the dual purpose of occupying the dead space in a syringe and further of lubricating the moement of the plunger within the barrel.

DESCRIPTION OF THE PRIOR ART

Probably the most commonly used instrument for blood gas samples is the standard hospital syringe. The needle in these syringes is first injected into an aqueous solution of anticoagulant such as heparin. Heparin is drawn into the syringe and then partially ejected. This eliminates the residual air in the dead space of the syringe and fills the residual dead space and the needle with liquid heparin. Thereafter, the syringe is injected into the artery. The arterial pressure (which may be as high as 200 mm of Hg) will push the syringe plunger outwardly, until stopped by the operator. Because of this many samples are too large. Furthermore, if there is not a tight fit of the plunger in the syringe barrel, excess blood under arterial pressure will squirt out of the syringe proper and onto the operator. Furthermore, if the operator becomes distracted or fails to stop the movement of the lunger outwardly, the plunger can be pushed almost entirely out of the syringe barrel thus losing the entire sample. This of course involves another "stick" for the patient, creates a housecleaning problem for the institution and generally is not desirable.

Various proposals have been made in the patent literature and in the commercial market to overcome these problems. Thus for example, Hatsuno, In U.S. Pat. No. 3,930,492 proposes a syringe having a stoper, which fits into a restricted portion of the syringe's proximal end, and which contains a rubber stopper at its proximal end. The stopper is pierced by a needle, which is contained in a holder, until it reaches the dead space, containing liquid heparin. The heparin is then evacuated through the needle proper thus evacuating any air from the syringe and filling the hollow shank of the needle with heparin and thus making the unit ready to take the sample. This blood sampling apparatus, sold under the trademark TERUMO, further involves the use of an adapter for the Blood Gas Analysis Machine. Therefore, it is necessary for the technicians to make a procedural change.

An arterial blood sampling unit has been proposed by Genese of Abbott Laboratories in U.S. Pat. No. 4,041,934. This apparatus is quite complicated and insofar as I am aware has not been put into commercial production. It involves a bayonet member in the syringe proper that punctures a membrane in the rear which membrane covers a chamber containing the heparin. The heparin is therefore injected through the bayonet, to the front of the syringe upon pushing the plunger proximally. As the plunger is depressed further, excess heparin is injected into the needle, which is attached onto the projecting neck of the syringe. Again, the arterial pressure of the blood will push the stopper 18 distally, until the proper size sample is taken.

Additionally, there has been introduced on the market, a unit sold by the Emde Corporation under the name of "MOSQUITO BLOOD GAS SAMPLER". This unit has been described in U.S. Pat. No. 4,133,304. The MOSQUITO BLOOD GAS SAMPLER utilizes capillary type blood collectors. Crystalline heparin in the barrel and the needle hub is utilized rather than an aqueous system. Again, the MOSQUITO system utilizes an air vent which is in the form of a mono-filament fishing line located between the barrel and a rubber stopper. Removal of the mono-filament line leaves sufficient vent in the stopper to evacuate air in the barrel. Nevertheless, even under perfect conditions, the blood comes into contact with the air in the syringe, as it is evacuated. Because the system does not always eliminate bubbles, the interior of the syringe and the stopper are siliconized making bubble retention minimal. Other difficulties encountered with the unit relate to the technique changes required of the therapist. Short fills are encountered, and once the mono-filament line has been removed, leaving the air vent between the stopper and the barrel wall, it is difficult, if not impossible, to apply subatmospheric pressure to the syringe to complete the sample.

Additionally, Marquest Medical Products, Inc. has introduced an apparatus called the "OMNISTIK" or "MINISTICK" which utilizes a similar technique.

A final apparatus on the market, known as the Deseret System utilizes a plunger with an axially disposed bore. This syringe utilizes a hydrophobic membrane, which upon first contact with the blood, closes the bore. Accordingly, it is necessary with this apparatus to hold the needle perpendicularly since an injection at an angle of 45° will result in a short fill and a rather large air bubble. Since most sticks or injections are made at about 45° rather than 90°, this creates a considerable technique problem. Furthermore, this apparatus also suffers from the fact that the blood sample itself evacuates residual air from the syringe barrel and thus offers an avenue of contamination of the sample through contact with the evacuated air.

BRIEF DESCRIPTION OF THE DRAWINGS

Referring now to the drawings.

DESCRIPTION OF THE PREFERRED EMBODIMENT

Figure 1:
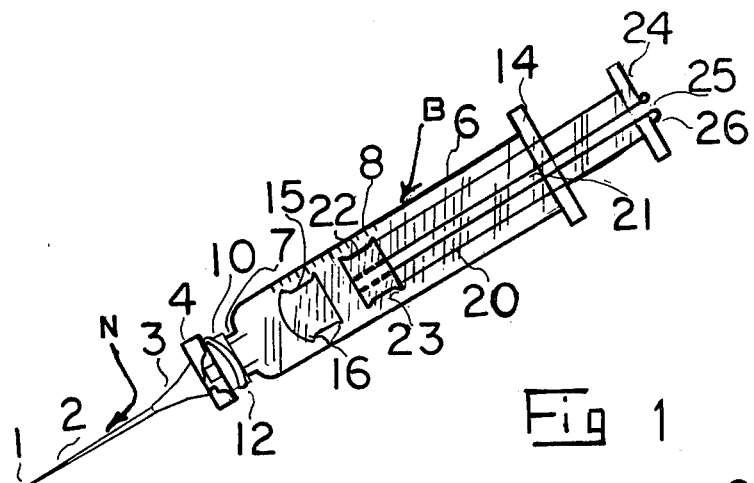
FIG. 1 is a view in elevation illustrating this invention.

Referring now to the drawings in detail, the needle "N" is of standard construction consisting of a point 1 a hollow shank 2 a plastic transparent hub 3 and a connecting collar 4. The syringe body consists of a transparent barrel B having a tubular portion 6 of uniform diameter containing calibrations 8 and which may be made of glass or plastic. A throw-away plastic barrel is contemplated for this particular invention.

At the proximal end of the barrel B, is a nozzle 7 of restricted diameter which has a projecting neck 10 for pressure fit with the hollow portion of the hub 3 of the needle N. A collar 11 is molded onto the projecting neck 10 and contains a large thread known as a LEUER LOCK, which engages with the connecting collar 4 of the hub 3 of the needle N.

The other end of the barrel B contains a laterally extending flange 14. For purposes of this application, the needle end of the syringe containing the nozzle portion and the projecting neck is referred to as the "proximal" end whereas the other end containing the circular laterally extending flange 14 is referred to as the "distal" end.

Inside of the barrel B proper there is located a floating stopper 15 preferably fabricated of rubber or an elastomeric polymer, containing extending sealing rings 16. The stopper is made so as to snugly fit against the interior walls of the tubular portion 6 of the barrel chamber, but allowing for smoother and effortless movement up and down the walls. The space between the floating stopper 15 and the restricted diameter portion of the nozzle 10 is referred to as 18 for convenience and the space between the distal end of the floating stopper 15 and the plunger 20 is designated as 19. The plunger 20 is axially disposed within the barrel B and contains an axially disposed gas channel or bore 21. Operatively connected to the end of the plunger 20 is a rubber stopper 22 containing sealing rings 23 which effectively seal the walls of the barrel with the plunger but allow easy reciprocating movement of the plunger 20 within the barrel B. It will be noted that the gas channel 21 extends through the rubber stopper 23 to communicate with the chamber 19 and opens through orifice 25 with the exterior part of the unit. An annular raised ring 26 is molded into the plunger and the plunger contains a laterally extending flange 24 which in the extended position of the plunger registers with the laterally extending flange 14 of the barrel.

As has previously been indicated, the purpose of this invention is to allow for sampling of arterial blood for purposes of blood gas analysis. As has previously been indicated, it is extremely desirable to collect the sample so that there is no contact of the arterial blood with air. Thus it is one of the goals of the invention to keep the chamber 18 between the proximal end of the stopper 15 and the restricted portion 7 of the nozzle as free of air as is possible. One of the objects of this invention then is to provide for methods wherein the dead space in chamber 18 is abvolutely devoid of air.

Figure 2:
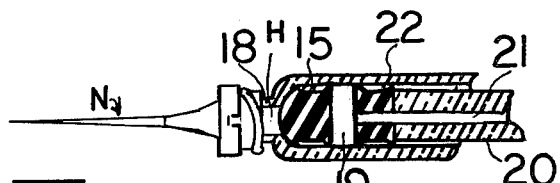
FIG. 2 is a fragmentary sectional view illustrating one modification of this invention.

As has been indicated, an anti-coagulent usually in the form of heparin H is usually utilized to prevent the blood being collected from coagulating in the shank 2 of the needle end or in the restricted portions of the syringe proper. As will be noted in FIG. 2, if the invention is utilized in a prepackaged stated, liquid heparin H can be prepackaged in the space 18 between the distal end of stopper 15 and the projecting neck 10 of the nozzle member.

Another method that can be utilized to incorporate the heparin into the dead space 18 of the syringe while filling the hollow shank of the needle 2 with the anti-coagulant and simultaneously evacuating any possible air from the chamber 18 is to inject the point 1 of the needle into a vial of sterile anti-coagulant which is usually available in hospitals, draw a small portion into the chamber 18, then invert the syringe, needle up, and expel the air and the residual heparin, leaving only heparin in the smalles portion of the dead space in chamber 18 and in the hollow shak 2 of the needle N proper.

The sample size is indicated by the calibrations 8. The calibratons 8 on the barrel B of the barrel take into consideration the displacement of the floating stopper 15. So by placing the proximal end of stopper 22 into place on the proper calibration for the desired sample, the needle N is injected into the artery by standard methods and the stopper 22 and plunger 20 acts as a stop for the proximal end of floating stopper 15 as the arterial blood pressure pushes the floating stopper distally thus simultaneously evacuating the air in chamber 19. By this method, the arterial blood does not come into contact with air at all. The technician can then inject the sample into the blood gas analysis machine or ice the sample for subsequent testing purposes.

As has been previously mentioned, the purpose of blood gas analysis is to evaluate the pneumatic function of the cardiovascular system. The measurements made through blood gas analysis are primarily the $PO_2$ and the $PCO_2$ concentrations of the arterial samples.

Contamination of the sample with air or incorporation of oxygen in any form into the sample tends to raise the $PO_2$ reading and also allows for loss of $CO_2$ into the air with a concomitant lowering of $PCO_2$ reading. Accordingly, the use of this system wherein the dead space 18 of the syringe body is either filled with prepackaged liquid heparin or is loaded with aqueous heparin and thereafter residual air is evacuated prior to the injection completely eliminates any contact of the arterial sample with oxygen or air. Furthermore, since the plunger 22 is preset at the desired sample level, it is possible to make a repeated samples without loss, without blood squirting around the stopper, and without contamination.

Figure 4:
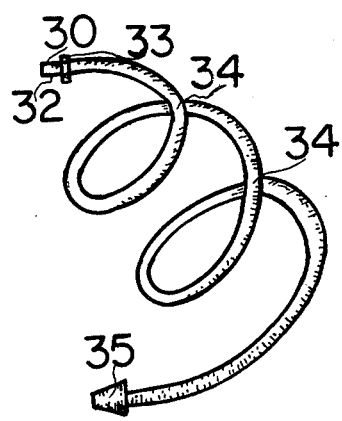
FIG. 4 illustrates a tubular adaptor which can be used with this invention.
Figure 5:
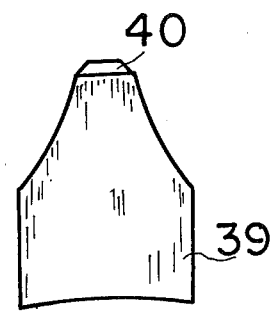
FIG. 5 illustrates a mouthpiece which can be used with the tubular adaptor of FIG. 4.
Figure 6:
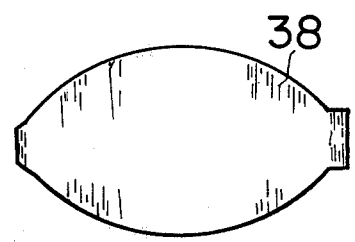
FIG. 6 is an aspirator bulb which can be utilized in conjunction with the tubular adaptor of FIG. 4.
Figure 7:
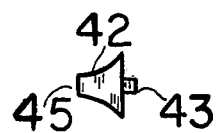
FIG. 7 is a stopper which can be used to close the gas channel of the plunger.

In many instances, however, the patient is in extremely critical condition. Thus, in shock cases or in coronary cases or post-operative cases, the blood pressure drops dramatically and in some cases not even register. In such instances it is essential to apply some subatmospheric pressure to the syringe in order to obtain the sample. Furthermore, through the use of this apparatus it is possible to make a two-handed injection where the arterial pressure is so low that it is difficult to even locate the blood vessel. In these cases, a tubular adaptor can be utilized. This is shown in FIG. 4 as tube 34 containing a connecting member 30. The connecting member consists of a hollow boss 32 of complimentary diameter to the gas channel 21 which can be fitted into the gas channel and has a flange 33 which acts as a stop. A hollow cone-shaped adaptor 35 at the other end readily fits to the mouth piece 39 or to the asirator bulb 38. In these cases, the proximal end of the plunger stopper 22 is set at the proper calibration, the injection is made. Subatmospheric pressure is applied either by suction applied by the mouth or through the aspirator bulb 38 by means of the tubular member 34. Thus the floating stopper 15 is drawn distally into abutment with the proximal end of the plunger stopper 22.

Figure 8:
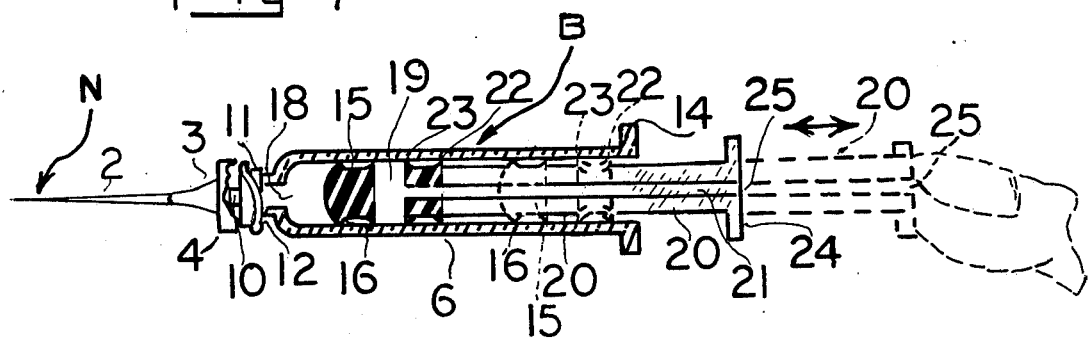
FIG. 8 illustrates in section with parts in elevation, this invention and shows in full lines the plunger and floating stopper in extended position and in phantom lines the plunger and floating stopper in retracted position.

In other instances, in cases of a short fill due to an obstruction in the shank 2 of the needle N or other problems it is necessary to aspirate the sample. This can be done quite easily by merely placing the finger over the end of the gas channel 21 as is shown in FIG. 8 and applying a reciprocating movement to the plunger 20. Due to Boyle's law, the pressure in chamber 19 is such that the floating stopper will move correspondingly to the plunger stopper 22. This is shown in the phantom lines. In any event, by aspiration of the plunger, after closing off the gas channel 21 by means of the finger, or through means of the stopper member 42, the sample can be aspirated until proper blood flow is resumed. The stopper member 42 consists of a solid boss 43 of complimentary diameter to the gas channel 21 a flange 44 and a nipple 43 for easy removal by the fingers.

Figure 3:
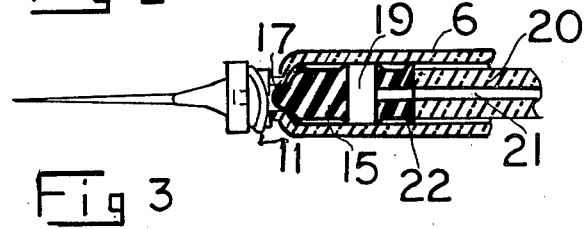
FIG. 3 illustrates another sectional view showing another modification of the invention.

Some technicians object to the use of aqueous heparin in taking the blood sample. These parties claim that air contamination is possibile through contact of the blood with the aqueous heparin solution. They have therefore proposed units with dried heparin on the barrels and in the needle shank 2 of the unit. This embodiment is contemplated through the use of this invention as is illustrated in FIG. 3. It will be noticed in FIG. 3 that the floating stopper 15 contains a projecting boss 17 which fills up most of the residual dead space 18 between the end of the floating stopper 15 and the projecting neck 10 of the syringe. In utilizing this apparatus, it is possible to preload the syringe with the liquid heparin, drive off the aqueous solution so that the unit is preheparinized, and utilize the projecting boss 17 of the floating stopper to minimize residual air in the dead space 18. The heparin does operate both to prevent coagulation of the blood and to serve to some extent as a lubricant for the stoppers 15 and 22 in the barrel of the syringe proper. With this modification, it is not always possible to eliminate all of the residual air. However, if the walls are siliconized, bubble retention is minimal. If a bubble does appear, inverting the syringe needle up, and tapping the barrel B with the finger will usually eliminate the bubble. Such minimal bubbles do not affect the readings appreciably, if the bubbles are eliminated immediately and are not allowed to be incorporated with the sample into the Blood-Gas Analysis machine.

Many modifications will appear to those skilled in the art from the detailed description hereinabove given which is meant to be exemplary in nature and non-limiting except so as to be commensurate in scope with the appended claims.

I claim:

1. A blood sampling unit comprising:
   A. a barrel member defining a substantially tubular member of uniform diameter and having:
      1. an internal wall section, and
      2. a proximal end of reduced internal diameter and including a projecting hollow neck;
   B. a hollow needle having a piercing end and an elongated hollow shank portion and a connecting hub for connection to said hollow neck of said barrel;
   C. a floating stopper having at least one peripheral sealing ring for rubbing engagement with the internal walls of said tubular member and for moving in either direction along the longitudinal axis of said tubular member;
   D. a plunger member having:
      1. sealing means for close sliding engagement with the interior walls of said barrel member and,
      2. a central gas channel extending axially through said plunger member, said gas channel opening directly into said barrel member and having an exterior orifice for introduction and evacuation of air.

2. A blood sampling unit, as defined in claim 1, in which the barrel member is made of a transparent material so as to immediately indicate the first flash of blood entering the sample chamber.

3. A blood sampling unit, as defined in claim 1, in which the hub of said needle is transparent so as to immediately indicate the first flash of blood entering the unit.

4. A blood sampling unit, as defined in claim 1, in which the sealing means of said plunger member includes a rubber stopper containing at least one sealing ring and having a centrally disposed gas channel registering with the gas channel of said plunger member.

5. A blood sampling unit, as defined in claim 1, the further combination therewith of an accessory comprising:
   A. a hollow connecting means for attachment to the proximal end of said gas channel of said plunger,
   B. a tubular member containing attacment means, and,
   C. a mouthpiece for attachment to said attachment means.

6. A blood sapling unit, as defined in claim 1, the further cmbination therewith which comprises:
   A. means for closing the orifice of the axially disposed gas channel at the distal end of said plunger.

7. A blood sampling unit, as defined in claim 6, in which said means for closing said orifice of the axially disposed gas channel is a rubber stopper with a projecting boss of complimentary diameter to the internal diameter of the gas channel.

* * * * *